United States Patent [19]

Maienfisch et al.

[11] Patent Number: 5,132,314
[45] Date of Patent: Jul. 21, 1992

[54] ANTHELMINTICS

[75] Inventors: Peter Maienfisch, Aesch; Christof Hildenbrand, Basel; Jean-Claude Gehret, Aesch, all of Switzerland

[73] Assignee: Ciba-Geigy Corporation, Ardsley, N.Y.

[21] Appl. No.: 783,433

[22] Filed: Oct. 25, 1991

Related U.S. Application Data

[62] Division of Ser. No. 586,176, Sep. 19, 1990, Pat. No. 5,081,125.

[30] Foreign Application Priority Data

Sep. 26, 1989 [CH] Switzerland .................. 3481/89

[51] Int. Cl.$^5$ .................. C07D 213/643; A01N 43/40
[52] U.S. Cl. ...................... 514/346; 514/344; 546/288; 546/291
[58] Field of Search ............ 514/346, 344; 546/288, 546/291

[56] References Cited

U.S. PATENT DOCUMENTS 4,946,854  8/1990  Maienfisch et al. .............. 514/346

FOREIGN PATENT DOCUMENTS 3523705  1/1987  Fed. Rep. of Germany .
865735   4/1961  United Kingdom .
876526   9/1961  United Kingdom .

OTHER PUBLICATIONS

Chemical Abstract, 104: 33896r (1986) Neubauer et al.
Maienfisch et al., Chemical Abstracts, vol. 115, entry 71636r (1991).

*Primary Examiner*—John M. Ford
*Attorney, Agent, or Firm*—Marla J. Mathias; Edward McC. Roberts

[57] ABSTRACT

Anthelmintically active compounds of formula I are described in which
$R_1$ is hydrogen, halogen, $C_1$-$C_2$alkyl, $C_1$-$C_2$thioalkyl, $C_1$-$C_2$haloalkyl, nitro, $C_1$-$C_2$alkoxy, or the group SO$_n$R in which R is $C_1$-$C_2$alkyl or phenyl and n is 0, 1 or 2;
$R_2$ is hydrogen, halogen, $C_1$-$C_2$alkyl, $C_1$-$C_2$haloalkyl, $C_1$-$C_2$haloalkoxy or $C_1$-$C_2$alkoxy;
$R_3$ is hydrogen or $C_1$-$C_2$alkyl;
$R_4$ is hydrogen or $C_1$-$C_2$alkyl;
$R_5$ is hydrogen, halogen or $C_1$-$C_5$alkyl;
$R_6$ is hydrogen, halogen or $C_1$-$C_5$alkyl;
$R_7$ is hydrogen, halogen, $C_1$-$C_2$alkyl, nitro, $C_1$-$C_2$haloalkyl, $C_1$-$C_2$haloalkoxy or $C_1$-$C_2$alkoxy;
$R_8$ is hydrogen, halogen, $C_1$-$C_2$alkyl, $C_1$-$C_2$haloalkyl, $C_1$-$C_2$haloalkoxy or $C_1$-$C_2$alkoxy;
$R_9$ is hydrogen, halogen, $C_1$-$C_2$alkyl, $C_1$-$C_2$haloalkyl, $C_1$-$C_2$haloalkoxy or $C_1$-$C_2$alkoxy;
$R_{10}$ is hydrogen, halogen, $C_1$-$C_6$alkyl, $C_1$-$C_2$haloalkyl, $C_1$-$C_2$alkylthio, $C_3$-$C_6$cycloalkyl or cyano;
$R_{11}$ is hydrogen, halogen, $C_1$-$C_6$alkyl, $C_1$-$C_2$haloalkyl, $C_1$-$C_2$alkylthio or $C_3$-$C_6$cycloalkyl;
$R_{12}$ is hydrogen or halogen; and
Y is =CH— or =N—; including the physiologically tolerable acid addition salts thereof, and also the preparation and use thereof and novel intermediates.

20 Claims, No Drawings

ANTHELMINTICS

This is a divisional of Ser. No. 586,176, filed Sep. 19, 1990, now U.S. Pat. No. 5,081,125, issued Jan. 14, 1992.

The present invention relates to novel substituted anthranilic acid derivatives having anthelmintic activity, to anthelmintic compositions based on those novel active ingredients and to the use of the active ingredients and compositions for controlling helminths, especially nematodes, cestodes and trematodes, in warm-blooded animals, especially mammals and preferably domestic animals and productive livestock. The invention also relates to the preparation of the active ingredients and compositions and to novel intermediates for the preparation of the active ingredients.

The novel anthranilic acid derivatives have the following formula I in which $R_1$ is hydrogen, halogen, $C_1$-$C_2$alkyl, $C_1$-$C_2$thioalkyl, $C_1$-$C_2$haloalkyl, nitro, $C_1$-$C_2$alkoxy, or the group $SO_nR$ in which R is $C_1$-$C_2$alkyl or phenyl and n is 0, 1 or 2;

$R_2$ is hydrogen, halogen, $C_1$-$C_2$alkyl, $C_1$-$C_2$haloalkyl, $C_1$-$C_2$haloalkoxy or $C_1$-$C_2$alkoxy;

$R_3$ is hydrogen or $C_1$-$C_2$alkyl;

$R_4$ is hydrogen or $C_1$-$C_2$alkyl;

$R_5$ is hydrogen, halogen or $C_1$-$C_5$alkyl;

$R_6$ is hydrogen, halogen or $C_1$-$C_5$alkyl;

$R_7$ is hydrogen, halogen, $C_1$-$C_2$alkyl, nitro, $C_1$-$C_2$haloalkyl, $C_1$-$C_2$haloalkoxy, or $C_1$-$C_2$alkoxy;

$R_8$ is hydrogen, halogen, $C_1$-$C_2$alkyl, $C_1$-$C_2$haloalkyl, $C_1$-$C_2$haloalkoxy or $C_1$-$C_2$alkoxy;

$R_9$ is hydrogen, halogen, $C_1$-$C_2$alkyl, $C_1$-$C_2$haloalkyl, $C_1$-$C_2$haloalkoxy or $C_1$-$C_2$alkoxy;

$R_{10}$ is hydrogen, halogen, $C_1$-$C_6$alkyl, $C_1$-$C_2$haloalkyl, $C_1$-$C_2$alkylthio, $C_3$-$C_6$cycloalkyl or cyano;

$R_{11}$ is hydrogen, halogen, $C_1$-$C_6$alkyl, $C_1$-$C_2$haloalkyl, $C_1$-$C_2$alkylthio or $C_3$-$C_6$cycloalkyl;

$R_{12}$ is hydrogen or halogen; and

Y is $=CH-$ or $=N-$; including the physiologically tolerable acid addition salts thereof.

To mention is a subgroup of compounds of the formula I in which $R_1$ is hydrogen, halogen, $C_1$-$C_2$alkyl, $C_1$-$C_2$haloalkyl, nitro, $C_1$-$C_2$alkoxy, or the group $SO_nR$ in which R is $C_1$-$C_2$alkyl or phenyl and n is 0, 1 or 2;

$R_2$ is hydrogen, halogen, $C_1$-$C_2$alkyl, $C_1$-$C_2$haloalkyl, $C_1$-$C_2$haloalkoxy or $C_1$-$C_2$alkoxy;

$R_3$ is hydrogen or $C_1$-$C_2$alkyl;

$R_4$ is hydrogen or $C_1$-$C_2$alkyl;

$R_5$ is hydrogen, halogen or $C_1$-$C_5$alkyl;

$R_6$ is hydrogen, halogen or $C_1$-$C_5$alkyl;

$R_7$ is hydrogen, halogen, $C_1$-$C_2$alkyl, nitro, $C_1$-$C_2$haloalkyl, $C_1$-$C_2$haloalkoxy or $C_1$-$C_2$alkoxy;

$R_8$ is hydrogen, halogen, $C_1$-$C_2$alkyl, $C_1$-$C_2$haloalkyl, $C_1$-$C_2$haloalkoxy or $C_1$-$C_2$alkoxy;

$R_9$ is hydrogen, halogen, $C_1$-$C_2$alkyl, $C_1$-$C_2$haloalkyl, $C_1$-$C_2$haloalkoxy or $C_1$-$C_2$alkoxy;

$R_{10}$ is hydrogen, halogen, $C_1$-$C_6$alkyl, $C_1$-$C_2$haloalkyl, $C_1$-$C_2$alkylthio, $C_3$-$C_6$cycloalkyl or cyano;

$R_{11}$ is hydrogen, halogen, $C_1$-$C_6$alkyl, $C_1$-$C_2$haloalkyl, $C_1$-$C_2$alkylthio or $C_3$-$C_6$cycloalkyl;

$R_{12}$ is hydrogen or halogen; and

Y is $=CH-$ or $=N-$; including the physiologically tolerable acid addition salts thereof.

By the term alkyl on its own or as a component of another substituent, depending on the number of carbon atoms indicated there is to be understood, within the scope of the present invention, for example the following straight-chain and branched groups: methyl, ethyl, n-propyl, isopropyl, n-butyl, sec.-butyl, tert.-butyl, isobutyl, etc.. Haloalkyl on its own or as a component of haloalkoxy is a mono- to per-halogenated alkyl substituent, such as, for example, $CH_2Cl$, $CHCl_2$, $CCl_3$, $CH_2F$, $CHF_2$, $CF_3$, $CH_2Br$, $CHBr_2$, $CBr_3$, $CH_2I$, $CI_3$, $CHClF$, $CHBrCl$, $CFBrCl$, $C_2F_5$, $CH_2CH_2Cl$, $CHClCH_3$, $C_2Cl_5$, $CHFCHCl_2$ etc., preferably $CF_3$. By halogen ther is to be understood throughout the specification fluorine, chlorine, bromine or iodine, preferably fluorine, chlorine or bromine, but more especially chlorine.

A preferred sub-group of compounds of formula I is formed by those compounds in which $R_1$, $R_2$, $R_3$, $R_4$, $R_7$, $R_8$, $R_9$, $R_{12}$ and Y are as defined for formula I;

$R_5$ is hydrogen, halogen or $C_1$-$C_3$alkyl;

$R_6$ is hydrogen, halogen or $C_1$-$C_3$alkyl;

$R_{10}$ is hydrogen, halogen, $C_1$-$C_4$alkyl, $C_1$-$C_2$haloalkyl, $C_1$-$C_2$alkylthio, cyclopropyl or cyano; and $R_{11}$ is hydrogen, halogen, $C_1$-$C_4$alkyl, $C_1$-$C_2$haloalkyl, $C_1$-$C_2$alkylthio or cyclopropyl; including the physiologically tolerable acid addition salts thereof.

A further preferred group is formed by compounds of formula I in which $R_1$ is hydrogen, halogen, methyl, methoxy or thiomethyl;

$R_2$ is hydrogen, methyl or halogen;

$R_3$ is hydrogen, methyl or ethyl;

$R_4$ is hydrogen, methyl or ethyl;

$R_5$ is hydrogen, halogen or $C_1$-$C_4$alkyl;

$R_6$ is hydrogen, halogen or $C_1$-$C_4$alkyl;

$R_7$ is hydrogen, halogen, methyl, methoxy, $CF_3$ or nitro;

$R_8$ is hydrogen or halogen;

$R_9$ is hydrogen, halogen, $C_1$-$C_2$alkyl, $C_1$-$C_2$haloalkyl, $C_1$-$C_2$haloalkoxy or $C_1$-$C_2$alkoxy;

$R_{10}$ and $R_{11}$, independently of one another, are each hydrogen, halogen, $C_1$-$C_4$alkyl, methylthio, trifluoromethyl, $CF_2CCl_2F$, cyclopropyl or cyano;

$R_{12}$ is hydrogen or halogen; and

Y is $=CH-$ or $=N-$, wherein the pyridinoxy or pyrimidinoxy substituent is bonded by way of the 3- or 4-position of the phenyl ring.

Other groups of preferred compounds of formula I are formed by those compounds in which $R_1$ is 5-halogen (preferably chlorine) or 4-halogen (preferably chlorine), $R_2$ is hydrogen and the remaining substituents are as defined for formula I or as defined in the above-mentioned preferred groups.

Within the scope of formula I and the mentioned sub-groups preference is given to those compounds in which the substituent $R_1$ is in the 5-position of the phenyl group.

Preferred compounds of formula I include the following individual compounds:

5-chloro-2-[(4-chlorophenylsulfonyl)-amino]-benzoic acid [4-(4-trifluoromethyl-6-cyclopropylpyrimidin-2-yloxy)-anilide];

5-chloro-2-[(4-chlorophenylsulfonyl)-amino]-benzoic acid [4-(3-chloro-5-trifluoromethylpyridin-2-yloxy)-anilide];

5-chloro-2-[(4-chlorophenylsulfonyl)-amino]-benzoic acid [4-(4-trifluoromethylpyridin-2-yloxy)-anilide];

5-chloro-2-[(4-chlorophenylsulfonyl)-amino]-benzoic acid [4-(4-trifluoromethyl-6-tert.-butylpyrimidin-2-yloxy)-anilide];

3,5-dichloro-2-[(4-chlorophenylsulfonyl)-amino]-benzoic acid [4-(4-trifluoromethyl-6-cyclopropylpyrimidin-2-yloxy)-anilide];

3,5-dichloro-2-[(4-chlorophenylsulfonyl)-amino]-benzoic acid [4-(5-trifluoromethylpyridin-2-yloxy)-anilide].

The preferred compounds also include 4-chloro-2-[(4-chlorophenylsulfonyl)-amino]-benzoic acid [4-(3-chloro-5-trifluoromethylpyridin-2-yloxy)-anilide].

It has been found that the novel compounds of formula I according to the invention surprisingly have a very favourable spectrum of activity against helminths that are parasites of animals, especially those that parasitise warm-blooded animals, especially mammals. The compounds of formula I can be used very successfully against nematodes as well as cestodes and trematodes. They are distinguished in particular by the fact that they are fully effective also against benzimidazole-resistant, especially thiabendazole-resistant, helminths ("thiabendazole" denotes the active ingredient 2-(thiazol-4-yl)-benzimidazole).

The compounds of formula I are prepared by (A) reacting a compound of formula II with a benzenesulfonic acid halide of formula III

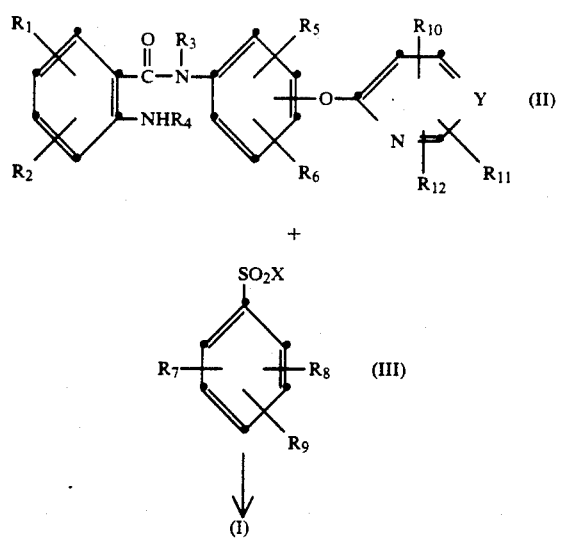

or (B) reacting a compound of formula IV with a compound of formula V

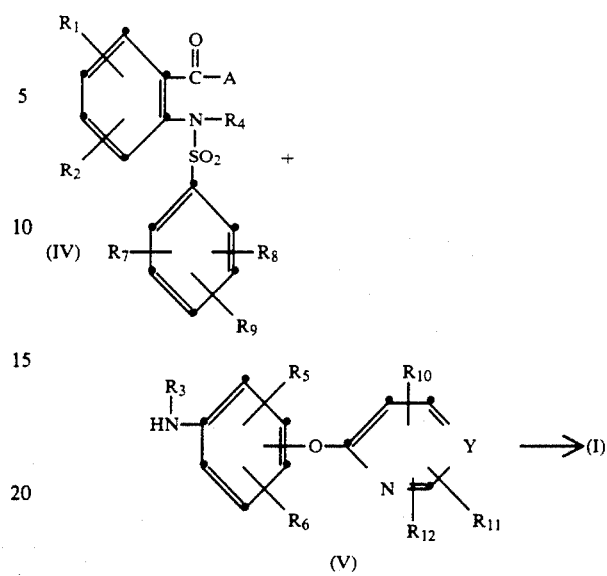

wherein the substituents $R_1$ to $R_{12}$ and Y in formulae II, III, IV and V are as defined for formula I, X in formula III is halogen, preferably chlorine or bromine, especially chlorine, and A in formula IV is halogen (preferably chlorine or bromine), OH, or a leaving group capable of reacting with an amino group, and, where appropriate, subsequently alkylating a compound of formula II in which both $R_3$ and $R_4$ are hydrogen or only one of them is hydrogen.

In the reactions (II) with (III) and (IV) with (V) there may be used as bases, for example, tertiary amines (such as triethylamine, trimethylamine, tripropylamine, N-methylpiperidine, 1,4-diazabicyclo(2,2,2)octane etc.), pyridine and pyridine bases (such as 4-dimethylaminopyridine, 4-pyrrolidylaminopyridine, picolines, lutidine etc.), and also alkaline earth metal or preferably alkali metal alcoholates of lower alkanols (such as, for example, sodium or potassium alcoholates of methanol, propanol, ethanol, n-butanol, isobutanol, tert.-butanol etc.). Pyridine is preferred.

Suitable solvents or diluents are, for example, the following aprotic solvents: aliphatic and aromatic hydrocarbons, such as benzene, toluene, xylenes, petroleum ether; halogenated hydrocarbons, such as chlorobenzene, methylene chloride, ethylene chloride, chloroform, carbon tetrachloride, tetrachloroethylene; ethers and ethereal compounds, such as dialkyl ethers (diethyl ether, diisopropyl ether, tert.-butylmethyl ether etc.), anisole, dioxane and tetrahydrofuran; nitriles, such as acetonitrile and propionitrile; some N,N-alkylated amides, such as dimethylformamide; dimethyl sulfoxide; ketones, such as acetone, diethyl ketone and methyl ethyl ketone, and mixtures of such solvents. In many cases the base itself can act as solvent.

The reaction temperatures are usually from $-20°$ to $+150°$ C., preferably from $0°$ to $+100°$ C. In cases where A in formula IV is OH, a condensation agent, such as dicyclohexylcarbodiimide, may be added.

The described preparation process, including all the subsidiary steps, forms an important component of the present invention.

The compounds of formula II are novel and the present invention relates to them since the main characteristics of the end products are already apparent in them.

The compounds of formula II can be prepared by several processes; for example they can be prepared from a compound of formula VI

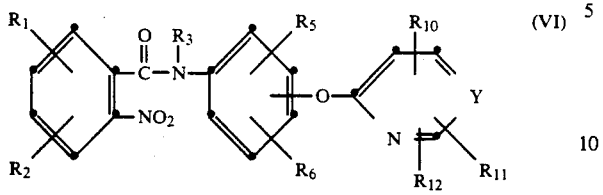

(i) by hydrogenation in the presence of a suitable hydrogenation catalyst and, where appropriate, by subsequent N-alkylation to introduce the substituent $R_4$, or
(ii) by chemical reduction, or
(iii) by reacting a compound of formula VII with a compound of formula V

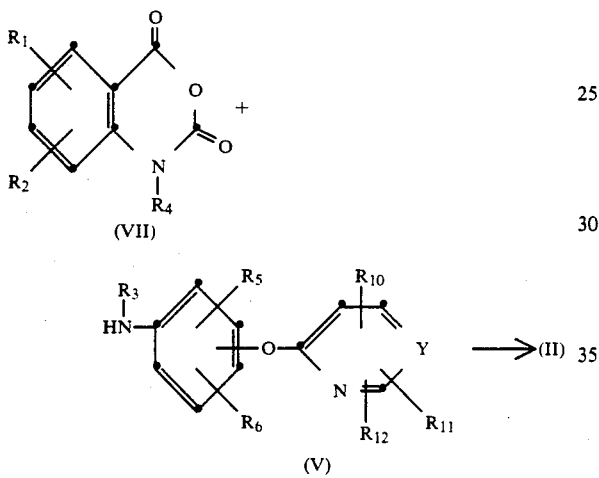

in which formulae the substituents $R_1$, $R_2$, $R_3$, $R_4$, $R_5$, $R_6$, $R_{10}$, $R_{11}$ and $R_{12}$ and Y are as defined for formula I.

The reactions (i) and (ii) can take place under normal pressure and are preferably carried out in the presence of an inert organic solvent or diluent, preferably in the presence of one of the above-mentioned ethers or ethereal compounds, an ester, such as ethyl acetate, propyl acetate or butyl acetate, or an alcohol, especially an alkanol, such as methanol, ethanol, propanol etc.. The reactions are generally carried out at temperatures of from 0° to 80° C., preferably from 10° to 50° C.

A suitable catalyst for process (i) is, for example, Rh/C or Raney nickel.

The chemical reduction (ii) can be carried out, for example, with Sn-(II)-chloride/HCl.

Reaction (iii) is preferably carried out in the presence of an inert organic polar solvent, such as N,N-dimethylformamide, N,N-dimethylacetamide, dimethyl sulfoxide, dioxane, butanone, THF or dimethoxyethane. The reaction temperatures are from −10° to +150° C., preferably from 0° to 100° C.

The nitro compounds of formula VI are also novel and the present invention relates to them.

Compounds of formula VI can be prepared by reacting compounds of formula VIII with compounds of formula (V)

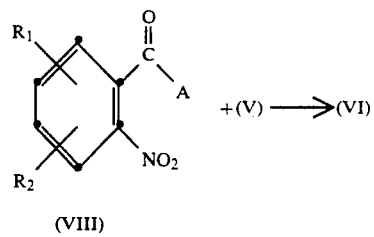

in which A in formula VIII is OH, a reactive leaving group, such as halogen (preferably chlorine or bromine), or an activated ester radical, such as, for example, alkoxycarbonyloxy. These reactions are preferably carried out in the presence of an inert organic solvent, such as benzene, toluene, $CH_2Cl_2$, ether, DMF, DMSO, THF, acetonitrile or acetone, advantageously in the presence of a base, such as triethylamine, pyridine or picoline, at from −20° C. to 150° C., preferably from 0° C. to 50° C. When A=OH, the reaction can also be carried out in the presence of a condensation agent, such as, for example, dicyclohexylcarbodiimide.

Compounds of formula V are known or can be prepared, for example, by reacting a compound of formula IX

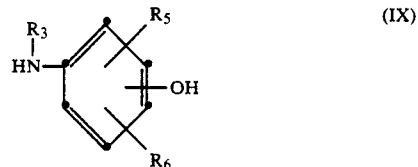

with a compound of formula X

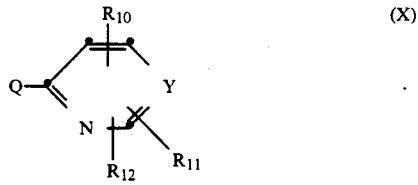

in which $R_3$, $R_5$, $R_6$, $R_{10}$, $R_{11}$ and $R_{12}$ and also Y are as defined for formula I and Q is a customary leaving group. The reaction temperatures are usually from 0° C. to 200° C., preferably from 10° C. to 150° C., and the reaction is carried out in inert polar solvents, such as, for example, N,N-dimethylformamide, N,N-dimethylacetamide or preferably dimethyl sulfoxide, with the addition of an inorganic base, such as sodium carbonate, potassium carbonate or, preferably, potassium hydroxide. The water of reaction formed in these reactions can be removed from the reaction mixture by means of an entrainer, such as, for example, $CH_2Cl_2$, toluene or benzene.

Q in formula X is either one of the customary leaving groups, for example halogen, especially chlorine, bromine or iodine; or a sulfonyloxy group, especially benzenesulfonyloxy, para-tosyloxy or lower alkylsulfonyloxy, preferably mesyloxy.

Compounds of formula VII are preferably obtained by oxidising compounds of formula XI

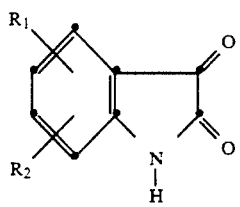 (XI)

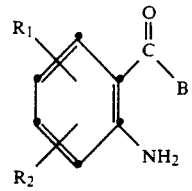 (XIV)

This preparation process is known, inter alia, from DE 29 25 175 and Angewandte Chemie 92, 196 (1980). The compounds of formula VII ($R_4$=H) obtained from such a process can, where appropriate, be alkylated at the nitrogen atom, for example according to J. Heterocycl. Chem. 565 (1975).

The compounds of formula XI and processes for their preparation are known, and they can be prepared according to a method familiar to the person skilled in the art, cf. Houben/Weyl vol. 7/4, p. 5 ff.

Compounds of formula IV (A=OH) can be obtained by hydrolysing compounds of formula XII or XIII

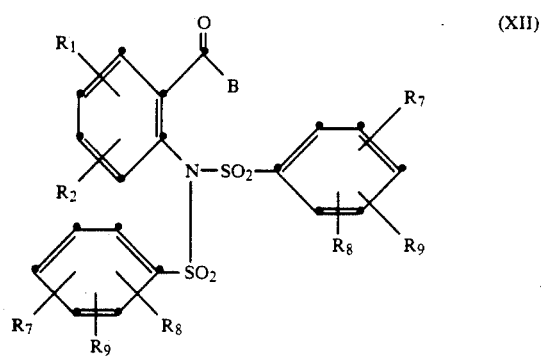 (XII)

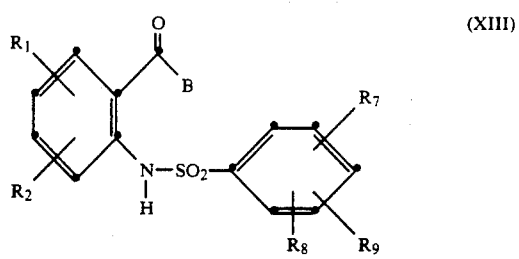 (XIII)

in which B is $OCH_3$ or $OC_2H_5$. The said hydrolysis is preferably effected with an inorganic base, such as NaOH or KOH, in the presence of a solvent, such as water and/or an alcohol, preferably methanol or ethanol, cf. Houben/Weyl, 9, p. 609 ff.

Compounds of formula IV (A=reactive leaving group) can be prepared according to methods familiar to the person skilled in the art, for example from compounds of formula IV (A=OH).

The compounds of formula XII are novel and the present invention extends also to them.

The compounds of formulae XII and XIII can be obtained by reacting compounds of formula XIV in which B, $R_1$ and $R_2$ are as defined hereinbefore, with compounds of formula III; when position 3 in compounds of formula XIV is occupied, mixtures of compounds of formula XII and XIII may result, although it is chiefly sulfonimides of formula XII that are obtained. When the 3-position in compounds of formula XIV is free, almost exclusively compounds of formula XIII are obtained. The said reactions are preferably carried out under the conditions indicated for reaction A (II+III→I).

The preparation of compounds of formula XIV can be carried out analogously to known methods, for example according to Tetrahedron 33, 217 (1977) and DE-3,001,579.

The starting compounds of formulae III, VIII, X, XI, XIII and XIV are known, or can be prepared analogously to the known compounds.

The invention also includes a method for the prophylactic protection of animals against parasitic helminths which comprises administering the compounds of formula I or the active ingredient formulations to the animals as an additive to feed or to drinks, or alternatively in solid or liquid form orally, by injection or by means of the pour-on method.

Of the endoparasites occurring in warm-blooded animals, it is specifically helminths that cause great damage. Animals infested by these parasites may not only suffer from retarded growth but may also have considerable physiological defects, which may even result in death. The development of therapeutic compositions that are suitable for controlling helminths and their stages of development and for providing protection against infestation by such parasites is therefore of great importance. Especially dangerous worm-related disorders are those brought about by nematodes, cestodes and trematodes parasitising the gastro-intestinal tract and other organs, especially in ruminants, such as sheep, cattle and goats, and also horses, pigs, red deer, dogs, cats and fowl.

The damage caused by helminthiases can be considerable where there is chronic and especially epidemic occurrence of worm-related disorders in herds of animals. The damage manifests itself inter alia in reductions in productivity, reduced resistance and increased mortality. Control and prevention of helminthiases is therefore seen as an urgent task in order to avoid or reduce such damage which is serious especially from the economic standpoint.

In the present description there is to be understood by the term "helminths" especially parasitic worms that belong to the Platyhelminthes (cestodes, trematodes) and Nemathelminthes (nematodes and related species), that is to say tapeworms, sucker worms and roundworms of the gastro-intestinal tract and other organs (for example liver, lungs, kidneys, lymph vessels, blood etc.). Although a number of substances having anthelmintic activity are known that have been proposed for controlling various species of helminth, these have not proved completely satisfactory either because at a tolerable dose it is not possible to make full use of their spectrum of activity or because at therapeutically effective doses they exhibit undesired side effects or properties. In this respect, the resistance to certain classes of substance occurring more and more today is also increasingly significant. For example, it is true that "Albendazol", which has been described in the literature (British Pat. No. 1464326; Am. J. Vet. Res. 38, 1425–1426 (1977); Am. J. Vet. Res. 37, 1515–1516 (1976); Am. J. Vet. Res. 38, 807–808 (1977); Am. J. Vet. Res. 38, 1247–1248 (1977)), has a limited spectrum of anthelmintic activity in ruminants. Its activity against benzimidazole-resistant nematodes and adult liver flukes, however, is unsatisfactory, since in particular the pathogenically important immature migrating forms of the latter are not affected by doses tolerated by the host animal.

It has surprisingly been found that the compounds of formula I not only, as has already been mentioned, have an intensive anthelmintic activity with a broad spectrum of action against nematodes, cestodes and trematodes, but also are favourable as regards their toxicity to warm-blooded animals.

The novel compounds of formula I according to the invention are suitable, for example, for controlling parasitic nematodes of the orders (according to K. I. Skrajabin), Rhabditida, Ascaridida, Spirurida, Trichocephalida, or for controlling cestodes of the orders (according to Wardle & McLeod), Cyclophyllidae, Pseudophyllidae, or for controlling trematodes of the order, Digenea, in domestic animals and productive livestock, such as cattle, sheep, goats, horses, pigs, cats, dogs and fowl. They may be administered to the animals either as a single dose or repeatedly, the single administrations preferably being from 1 to 500 mg per kg of body weight depending on the species of animal. Protracted administration in many cases results in an improved action or may permit the use of smaller total doses.

The compositions according to the invention are prepared by so bringing the compounds of formula I into contact with liquid and/or solid formulation adjuvants by mixing and/or grinding in stages that an optimum display of the anthelmintic activity of the formulation, conformable to the application, is achieved.

The formulation stages can be supplemented by kneading, granulating (granulates) and optionally compressing (pellets).

Suitable formulation adjuvants are, for example, solid carriers, solvents and, where appropriate, surface-active substances (surfactants).

The following formulation adjuvants are used to prepare the compositions according to the invention: solid carriers such as, for example, kaolin, talcum, bentonite, sodium chloride, calcium phosphate, carbohydrates, cellulose powder, cottonseed meal, polyethylene glycol ether, where appropriate, binders such as, for example, gelatin, soluble cellulose derivatives, if desired with the addition of surface-active substances, such as ionic or non-ionic dispersants; and also natural mineral fillers, such as calcite, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant material.

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil, and water.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil.

Frequently, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable as formulation adjuvants are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8-C_{22}$alkyl radical and, as further substituents, unsubstituted or halogenated lower alkyl, benzyl or hydroxylower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described, inter alia, in the following publications:

"Mc Cutcheon's Detergents and Emulsifiers Annual", MC Publishing Corp., Ridgewood, N.J., 1981;

Stache, H., "Tensid-Taschenbuch", Carl Hanser Verlag, Munich/Vienna, 1981.

Suitable binders for tablets and boli are chemically modified natural polymer substances that are soluble in water or alcohol, such as starch, cellulose or protein derivatives (e.g. methylcellulose, carboxymethylcellulose, ethylhydroxyethylcellulose, proteins such as zein, gelatin and the like) and synthetic polymers, such as, for example, polyvinyl alcohol, polyvinylpyrrolidone etc. The tablets also contain fillers (e.g. starch, microcrystalline cellulose, sugar, lactose, etc.), glidants and disintegrators.

If the anthelmintic compositions are in the form of feed concentrates, then the carriers used are, for example, performance feed, feed grain or protein concentrates. In addition to the active ingredients, such feed concentrates or compositions may contain additives, vitamins, antibiotics, chemotherapeutic agents or pesticides, especially bacteriostatics, fungistatics or coccidiostatics, or also hormone preparations, substances having an anabolic activity, or substances that promote growth, influence the meat quality of slaughtered animals or are useful to the organism in some other way. If the compositions or the active ingredients of formula I contained therein are added directly to the feed or to the herd drinks, then the prepared feed or the prepared drink preferably contains the active ingredients in a concentration of approximately from 0.0005 to 0.02 percent by weight (5-200 ppm).

The compositions according to the invention can be administered to the animals to be treated perorally, parenterally, subcutaneously or topically, the compositions being in the form of solutions, emulsions, suspensions (drenches), powders, tablets, boli and capsules.

The anthelmintic compositions according to the invention generally contain from 0.1 to 99% by weight, preferably from 0.1 to 95% by weight, of a compound of formula I, and from 99.9 to 1% by weight, preferably from 99.9 to 5% by weight, of a solid or liquid adjuvant, including from 0 to 25% by weight, preferably from 0.1 to 25% by weight, of a surfactant.

Whereas commercial products will preferably be formulated as concentrates, the end user will normally employ dilute formulations.

The compositions may also contain further auxiliaries such as stabilisers, antifoams, viscosity regulators, binders, tackifiers as well as other active ingredients for obtaining special effects.

The present invention relates also to such anthelmintic compositions employed by the end user.

The following Examples serve to illustrate the invention without implying any limitation thereof.

1. PREPARATION EXAMPLES IN ACCORDANCE WITH PROCESS A 1.1 Preparation of
5-chloro-2-[(4-chlorophenylsulfonyl)-amino]-benzoic acid
[4-(3-chloro-5-trifluoromethylpyridyl-2-oxy)-anilide]

(a) 5-Chloro-2-nitrobenzoyl chloride

A mixture of 80.6 g of 5-chloro-2-nitrobenzoic acid and 58.2 ml of thionyl chloride is heated at 90° C. for 2 hours. The excess thionyl chloride is then distilled off in vacuo. 87.1 g of 5-chloro-2-nitrobenzoyl chloride are obtained.

(b) 5-Chloro-2-nitrobenzoic acid
[4-(3-chloro-5-trifluoromethylpyridyl-2-oxy)-anilide]

A solution of 8.0 g of 4-(3-chloro-5-trifluoromethylpyridyl-2-oxy)-aniline and 5.2 ml of triethylamine in 50 ml of methylene chloride is added dropwise, at 0° C., to a solution of 5.8 g of 5-chloro-2-nitrobenzoyl chloride in 50 ml of methylene chloride. After the mixture has been stirred at room temperature for 2 hours, approximately 80% of the solvent is removed in a rotary evaporator. The resulting crystal mass is stirred with 100 ml of diethyl ether, and the resulting crystals are washed with 1N HCl solution and $H_2O$ and are again stirred with 100 ml of diethyl ether. 9.6 g of 5-chloro-2-nitrobenzoic acid [4-(3-chloro-5-trifluoromethylpyridyl-2-oxy)-anilide] having a melting point of 216°–218° C. are obtained.

(c) 2-Amino-5-chlorobenzoic acid
[4-(3-chloro-5-trifluoromethylpyridyl-2-oxy)-anilide]

8.0 g of 5-chloro-2-nitrobenzoic acid [4-(3-chloro-5-trifluoromethylpyridyl-2-oxy)-anilide] are dissolved in 90 ml of tetrahydrofuran and the solution is hydrogenated for 6 hours at room temperature under a hydrogen atmosphere in the presence of 4 g of 5% rhodium/carbon. The reaction mixture is then filtered and the solvent is removed by distillation. The resulting crude product is stirred with diethyl ether. 5.5 g of 2-amino-5-chlorobenzoic acid [4-(3-chloro-5-trifluoromethylpyridyl-2-oxy)-anilide] are obtained in the form of white crystals (m.p. 180°–184° C.).

(d)
5-Chloro-2-[(4-chlorophenylsulfonyl)-amino]-benzoic acid
[4-(3-chloro-5-trifluoromethylpyridyl-2-oxy)-anilide]

2.0 g of 4-chlorobenzenesulfonic acid chloride are added to a solution of 3.8 g of 5-chloro-2-aminobenzoic acid [4-(3-chloro-5-trifluoromethylpyridyl-2-oxy)-anilide] in 8.6 ml of pyridine at 0° C. After the reaction mixture has been stirred for 16 hours at room temperature, 300 ml of methylene chloride are added and the resulting solution is then washed with 100 ml each of 1N HCl, $H_2O$, saturated $NaHCO_3$ solution and saturated NaCl solution. The organic phase is then dried with $MgSO_4$ and concentrated by evaporation. The crude product obtained is purified by stirring in diethyl ether. In this manner 3.8 g of 5-chloro-2-[(4-chlorophenylsulfonyl)-amino]-benzoic acid [4-(3-chloro-5-trifluoromethylpyridyl-2-oxy)-anilide] are obtained in the form of white crystals (m.p. 191°–193° C.).

IN ACCORDANCE WITH PROCESS B

2.1. Process for the preparation of 3,5-dichloro-2-[(4-chlorophenylsulfonyl)-amino]-benzoic acid [4-(4-trifluoromethyl-6-cyclopropylpyrimidin-2-yloxy)-anilide]

(a) 3,5-Dichloro-2-[di-(4-chlorophenylsulfonyl)-amino]-benzoic acid ethyl ester 138.0 g of 4-chlorobenzenesulfonic acid chloride are added in portions, at room temperature, to a solution of 50.0 g of 3,5-dichloroanthranilic acid ethyl ester in 210 ml of dry pyridine. The reaction mixture is heated to 80°–90° C. and stirred for 28 hours at that temperature to complete the reaction. After cooling, the reaction mixture is poured onto ice/water and acidified with 2N hydrochloric acid. The sticky, oily precipitate is dissolved in diethyl ether, and the aqueous phase is removed. The organic phase is washed with water and saturated sodium chloride solution. After drying over magnesium sulfate, the ether is evaporated off and the crystals remaining are stirred in a mixture of diethyl ether/hexane 4:1. The crystals, which are filtered off, weigh 87.3 g after drying and correspond to the title compound (m.p. 148°–150° C.).

(b) 3,5-Dichloro-2-[(4-chlorophenylsulfonyl)-amino]-benzoic acid

A suspension of 27.0 g of 3,5-dichloro-2-[di-(4-chlorophenylsulfonyl)-amino]-benzoic acid ethyl ester, 139 ml of 2N sodium hydroxide solution and 140 ml of ethanol is boiled at reflux for 6 hours, the solid gradually dissolving. After the reaction mixture has cooled, the precipitated crystals are filtered off and dissolved in 400 ml of water. 400 ml of methanol are added, acidification with 2N hydrochloric acid is carried out, and the precipitated crystals are filtered off. 12.3 g of the title compound (m.p. 188°–190° C.) are obtained.

(c) 3,5-Dichloro-2-[(4-chlorophenylsulfonyl)-amino]-benzoic acid [4-(4-trifluoromethyl-6-cyclopropylpyrimidin-2-yloxy)-anilide]

4.0 g of 3,5-dichloro-2-[(4-chlorophenylsulfonyl)-amino]-benzoic acid are suspended in 10 ml of thionyl chloride. The reaction mixture is boiled at reflux for 3 hours. After the excess thionyl chloride has been distilled off, the residue is twice concentrated by evaporation from 20 ml of toluene. The solid crude acid chloride so obtained is dissolved in 30 ml of methylene chloride. A solution of 3.3 g of 4-(4-trifluoromethyl)-6-cyclopropylpyrimidin-2-yloxy)-aniline [m.p. 75°–78° C.], 2 ml of triethylamine and 20 ml of methylene chloride is slowly added dropwise to this solution while cooling with ice/water. After 24 hours at room temperature, the precipitated solid is filtered off and washed with a small amount of methylene chloride. The crude product is washed with 2N hydrochloric acid and water, then dried and stirred with 50 ml of diethyl ether. 2.27 g of the title compound (m.p. 273°–276° C.) are obtained. It is possible to isolate a further 2.06 g of the title compound by working up the concentrated mother liquors in the above manner.

The compounds listed in the following can be prepared analogously to the described methods. The lists are not of a limiting nature.

TABLE 1
Compounds of formula Ia
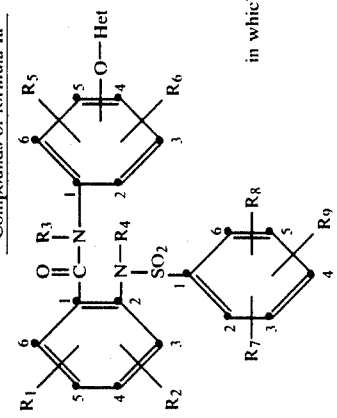
in which $R_9$ is hydrogen.
| Comp. No. | $R_1$ | $R_2$ | $R_3$ | $R_4$ | $R_5$ | $R_6$ | $R_7$ | $R_8$ | Position of Het | Het | M.p. [°C.] | Preparation variant |
|---|---|---|---|---|---|---|---|---|---|---|---|---|
| 1.1 | 5-Cl | H | H | H | H | H | 4-Cl | H | 4 | (CF₃, N, cyclopropyl pyrimidine) | 199–201 | A |
| 1.2 | 5-Cl | H | H | H | H | H | 4-Cl | H | 4 | (Cl, CF₃ pyridine) | 191–193 | A |
| 1.3 | 5-Cl | H | H | H | H | H | 4-Cl | H | 4 | (CF₃ pyridine) | 162–165 | A |
| 1.4 | 5-Cl | H | H | H | H | H | 4-Cl | H | 4 | (CF₃, N, C₄H₉-t pyrimidine) | 203–204 | A |

TABLE 1-continued
Compounds of formula Ia
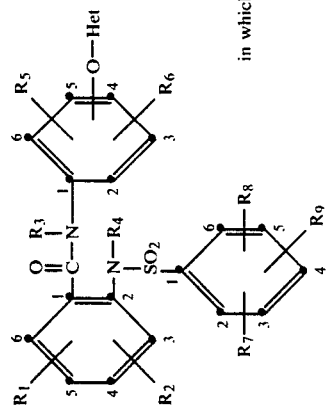
in which $R_9$ is hydrogen.
| Comp. No. | $R_1$ | $R_2$ | $R_3$ | $R_4$ | $R_5$ | $R_6$ | $R_7$ | $R_8$ | Position of Het | Het | M.p. [°C] | Preparation variant |
|---|---|---|---|---|---|---|---|---|---|---|---|---|
| 1.5 | 5-Cl | 3-Cl | H | H | H | H | 4-Cl | H | 4 | (CF₃, N, cyclopropyl pyrimidine) | 273–276 | B |
| 1.6 | 5-Cl | 3-Cl | H | H | H | H | 4-Cl | H | 4 | (CF₃, Cl, N pyridine) | 285–286 | B |
| 1.7 | 5-SCH₃ | H | H | H | H | H | 4-Cl | H | 4 | (CF₃, N, cyclopropyl pyrimidine) | 167–170 | A |

TABLE 1-continued
Compounds of formula Ia
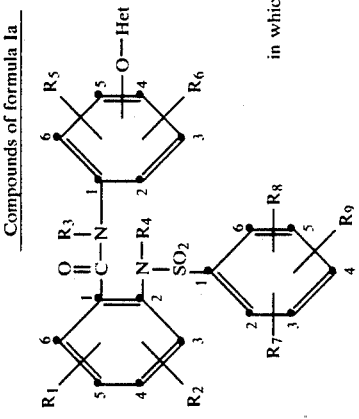
in which $R_9$ is hydrogen.
| Comp. No. | $R_1$ | $R_2$ | $R_3$ | $R_4$ | $R_5$ | $R_6$ | $R_7$ | $R_8$ | Position of Het | Het | M.p. [°C.] | Preparation variant |
|---|---|---|---|---|---|---|---|---|---|---|---|---|
| 1.8 | 5-Cl | H | H | H | H | H | 4-NO$_2$ | H | 4 | | | A |
| 1.9 | 6-CH$_3$ | 3-OCH$_3$ | H | H | H | H | 4-Cl | H | 4 | | | A |
| 1.10 | 5-Cl | H | H | H | H | H | 4-Cl | H | 4 | | | A |
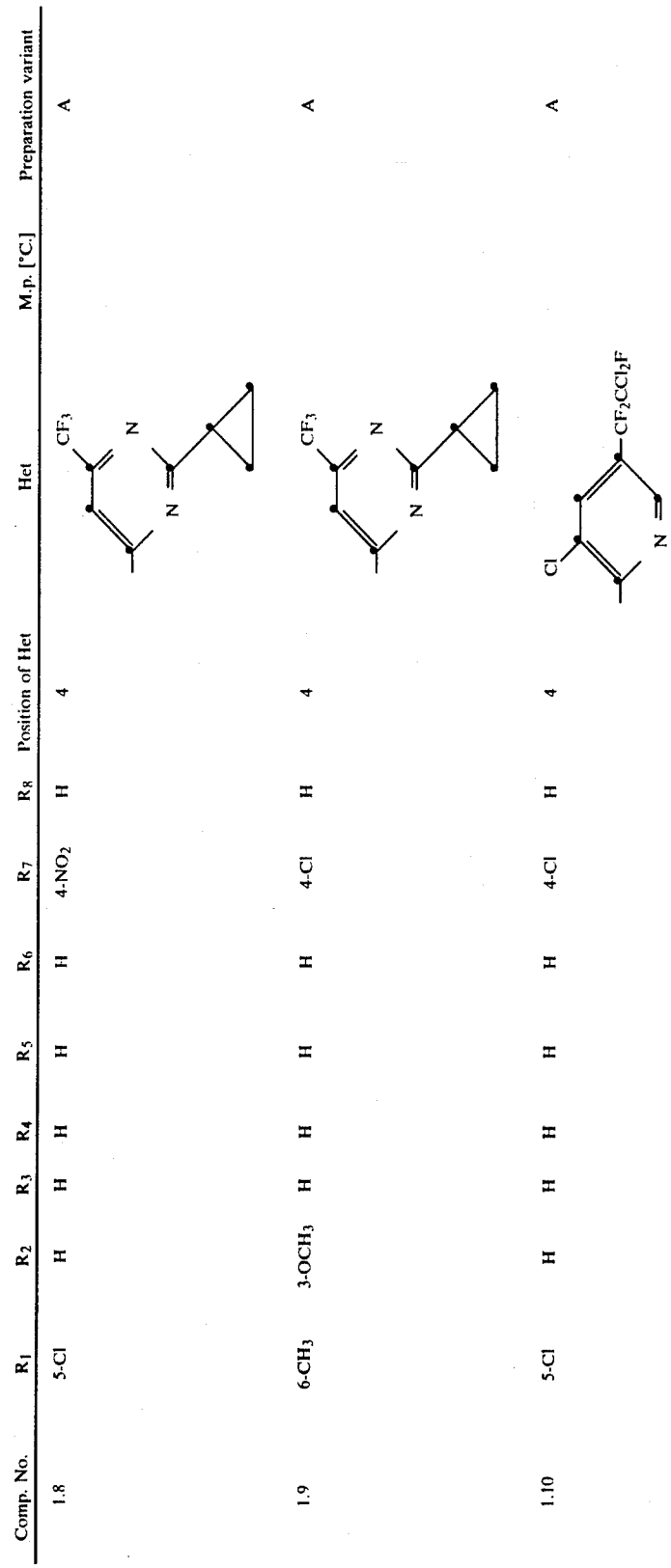

TABLE 1-continued
Compounds of formula Ia in which $R_9$ is hydrogen.

| Comp. No. | $R_1$ | $R_2$ | $R_3$ | $R_4$ | $R_5$ | $R_6$ | $R_7$ | $R_8$ | Position of Het | Het | M.p. [°C.] | Preparation variant |
|---|---|---|---|---|---|---|---|---|---|---|---|---|
| 1.11 | 5-Cl | 3-Cl | H | H | H | H | 4-Cl | H | 4 | (F, Cl pyridine) | 258–260 | B |
| 1.12 | 5-Cl | 3-Cl | H | H | H | H | 4-Cl | H | 4 | (CN, CH₃, CF₃ pyridine) | 309–312 | B |
| 1.13 | 5-Cl | 3-Cl | H | H | H | H | 4-Cl | H | 4 | (CH₃, SCH₃ pyrimidine) | 264–265 | B |
| 1.14 | 5-Cl | 3-Cl | H | H | H | H | 4-Cl | H | 4 | (pyridine) | 228–231 | B |

TABLE 1-continued
Compounds of formula Ia
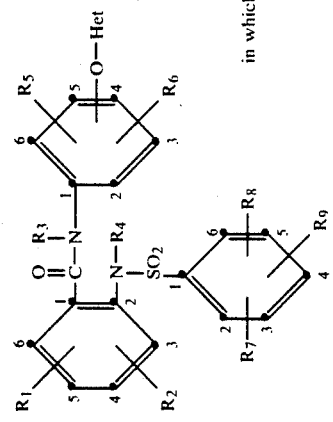
in which R9 is hydrogen.
| Comp. No. | R1 | R2 | R3 | R4 | R5 | R6 | R7 | R8 | Position of Het | Het | M.p. [°C.] | Preparation variant |
|---|---|---|---|---|---|---|---|---|---|---|---|---|
| 1.15 | 5-Cl | 3-Cl | H | H | 2-isopropyl | H | 4-Cl | H | 4 | | 250–252 | B |
| 1.16 | 5-Cl | 3-Cl | H | H | H | 6-CH$_3$ | 4-Cl | H | 4 | | 282–285 | B |
| 1.17 | 5-Cl | 3-Cl | H | H | 2-CH$_3$ | H | 4-Cl | H | 4 | | 264–266 | B |
| 1.18 | 5-Cl | 3-Cl | H | H | H | H | 4-Cl | H | 4 | | 256–259 | B |

TABLE 1-continued
Compounds of formula Ia
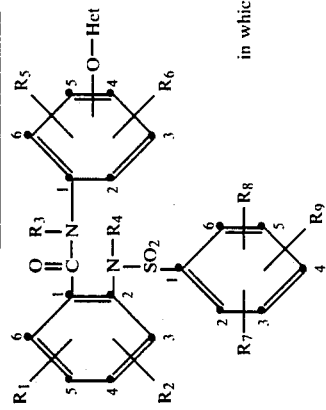
in which R9 is hydrogen.
| Comp. No. | R1 | R2 | R3 | R4 | R5 | R6 | R7 | R8 | Position of Het | Het | M.p. [°C.] | Preparation variant |
|---|---|---|---|---|---|---|---|---|---|---|---|---|
| 1.19 | 5-Cl | H | H | H | H | H | 4-Cl | H | 4 | CF3, Cl pyridine | 175–177 | B |
| 1.20 | 5-CF3 | H | H | H | H | H | 4-Cl | H | 4 | CF3, Cl pyridine | | B |
| 1.21 | 3-CF3 | H | H | H | H | H | 4-Cl | H | 4 | CF3, Cl pyridine | 278–281 | A |
| 1.22 | 4-OCH3 | 6-CH3 | H | H | H | H | 4-Cl | H | 4 | CF3, cyclopropyl pyridine | | B |

TABLE 1-continued
Compounds of formula Ia in which R$_9$ is hydrogen.

| Comp. No. | R$_1$ | R$_2$ | R$_3$ | R$_4$ | R$_5$ | R$_6$ | R$_7$ | R$_8$ | Position of Het | Het | M.p. [°C.] | Preparation variant |
|---|---|---|---|---|---|---|---|---|---|---|---|---|
| 1.23 | 5-S(O)CH$_3$ | H | H | H | H | H | 4-Cl | H | 4 | Cl-pyridine-CF$_3$ | | Subsequent oxidation |
| 1.24 | 5-SO$_2$CH$_3$ | H | H | H | H | H | 4-Cl | H | 4 | Cl-pyridine-CF$_3$ | | Subsequent oxidation |
| 1.25 | 5-SCH$_3$ | H | H | H | H | H | 4-Cl | H | 4 | Cl-pyridine-CF$_3$ | 158-161 | A |
| 1.26 | 5-F | H | H | H | H | H | 4-Cl | H | 4 | Cl-pyridine-CF$_3$ | 218-220 | A |

TABLE 1-continued
Compounds of formula Ia
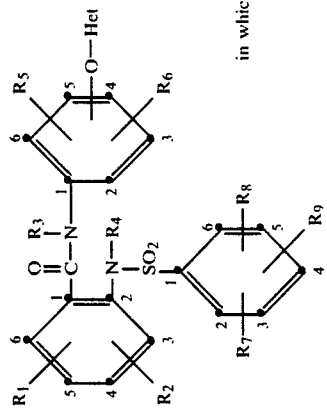
in which R₉ is hydrogen.
| Comp. No. | $R_1$ | $R_2$ | $R_3$ | $R_4$ | $R_5$ | $R_6$ | $R_7$ | $R_8$ | Position of Het | Het | M.p. [°C.] | Preparation variant |
|---|---|---|---|---|---|---|---|---|---|---|---|---|
| 1.27 | 5-F | 3-F | H | H | H | H | 4-Cl | H | 4 | Cl-pyridyl-CF₃ | 278–279 | A |
| 1.28 | 5-Cl | 3-Cl | H | H | H | H | 4-Cl | H | 4 | pyridyl-NO₂ | 258–261 | B |
| 1.29 | 5-Cl | 3-Cl | H | H | 4-CH₃ | H | 4-Cl | H | 3 | pyrimidyl-CF₃,CH₃ | 244–246 | B |
| 1.30 | 5-Cl | H | CH₃ | H | H | H | 4-Cl | H | 4 | Cl-pyridyl-CF₃ | 169–170 | B |

TABLE 1-continued

Compounds of formula Ia in which R9 is hydrogen.

| Comp. No. | R1 | R2 | R3 | R4 | R5 | R6 | R7 | R8 | Position of Het | Het | M.p. [°C.] | Preparation variant |
|---|---|---|---|---|---|---|---|---|---|---|---|---|
| 1.31 | 5-Cl | H | H | H | 2-F | H | 4-Cl | H | 4 | (Cl, CH3, CF3-pyridine) | 145–147 | B |
| 1.32 | 5-Cl | H | H | CH3 | 2-F | H | 4-Cl | H | 4 | (CF3, CH3-pyridine, cyclopropyl) | 155–157 | B |
| 1.33 | 5-Cl | H | H | H | H | H | 4-Cl | H | 4 | (Cl, CH3, CF3-pyridine) | 176–178 | A |
| 1.34 | 5-Cl | H | H | H | H | H | 4-Cl | 3-Cl | 4 | (Cl, CH3, CF3-pyridine) | | A |

TABLE 1-continued

Compounds of formula Ia

[Structure: benzene ring with R1 at 5, R2 at 4, and substituent at 1 being C(=O)-N(R3)- connected to a second benzene ring bearing R4, with N-SO2- linkage to a third benzene ring bearing R7, R8, R9 positions; and O-Het group with R5, R6 substituents]

in which R9 is hydrogen.

| Comp. No. | R1 | R2 | R3 | R4 | R5 | R6 | R7 | R8 | Position of Het | Het | M.p. [°C] | Preparation variant |
|---|---|---|---|---|---|---|---|---|---|---|---|---|
| 1.35 | 5-Cl | H | H | H | 4-Cl | H | 4-Cl | H | 3 | chloro-methyl-pyridine-CF3 | 188–190 | A |
| 1.36 | 5-Cl | H | H | H | 4-Cl | H | 4-F | H | 3 | chloro-methyl-pyridine-CF3 | 214–218 | A |
| 1.37 | 5-OCH3 | H | H | H | H | H | 4-Cl | H | 4 | cyclopropyl-pyrimidine-CF3 | | B |

TABLE 1-continued
Compounds of formula Ia
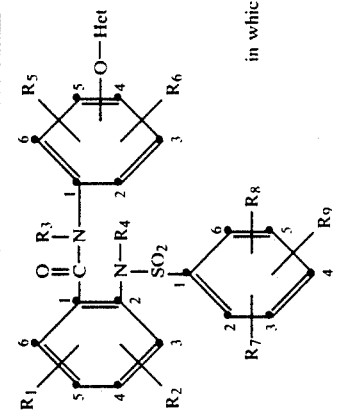
in which R₉ is hydrogen.
| Comp. No. | $R_1$ | $R_2$ | $R_3$ | $R_4$ | $R_5$ | $R_6$ | $R_7$ | $R_8$ | Position of Het | Het | M.p. [°C.] | Preparation variant |
|---|---|---|---|---|---|---|---|---|---|---|---|---|
| 1.38 | 5-Cl | H | H | H | H | H | 4-OCH₃ | H | 4 | (CF₃, N, cyclopropyl) | | A |
| 1.39 | 4-Cl | H | H | H | H | H | 4-Cl | H | 4 | (CF₃, Cl, N) | 197–200 | B |
| 1.40 | 6-CH₃ | H | H | H | H | H | 4-CH₃ | H | 4 | (CF₃, N, cyclopropyl) | 207–211 | B |

TABLE 1-continued
Compounds of formula Ia
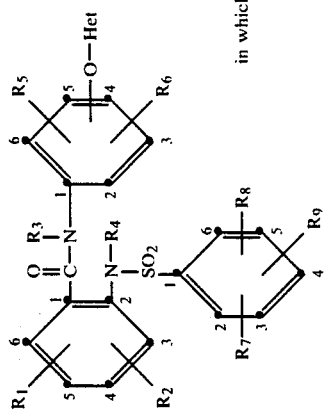
in which R9 is hydrogen.
| Comp. No. | R1 | R2 | R3 | R4 | R5 | R6 | R7 | R8 | Position of Het | Het | M.p. [°C.] | Preparation variant |
|---|---|---|---|---|---|---|---|---|---|---|---|---|
| 1.41 | 5-F | H | H | H | H | H | 4-Cl | H | 4 | 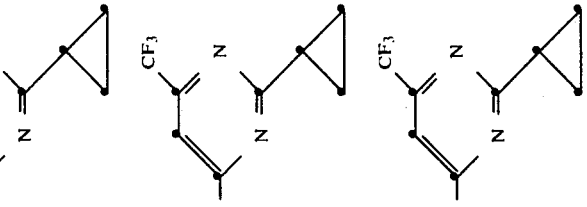 | 231–233 | A |
| 1.42 | 5-F | 3-F | H | H | H | H | 4-Cl | H | 4 | 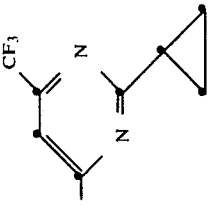 | 245–247 | A |
| 1.43 | 5-Cl | 4-Cl | H | H | H | H | 4-Cl | H | 4 | 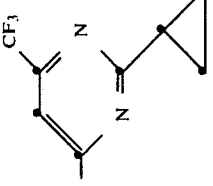 | | |

TABLE 2
Intermediates of formula
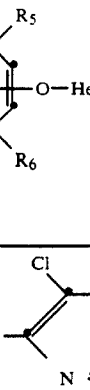
| Comp. No. | $R_1$ | $R_2$ | $R_3$ | $R_4$ | $R_6$ | $R_5$ | Position of Het | Het | M.p. [°C.] |
|---|---|---|---|---|---|---|---|---|---|
| 2.1 | 5-Cl | H | H | H | H | H | 4 | 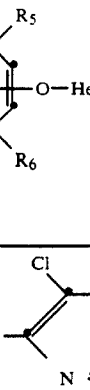 | 180–184 |
| 2.2 | 5-Cl | H | H | H | H | H | 4 | 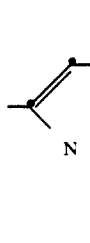 | 175–177 |
| 2.3 | 5-Cl | H | H | H | H | H | 4 |  | 182–183 |
| 2.4 | 5-Cl | H | H | H | H | H | 4 | 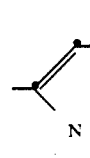 | 173–174 |
| 2.5 | 5-Cl | H | H | $CH_3$ | H | H | 4 | 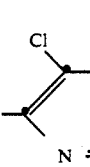 | 190–192 |
| 2.6 | 4-Cl | H | H | H | H | H | 4 | 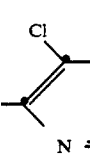 | 218–220 |
| 2.7 | 5-$SCH_3$ | H | H | H | H | H | 4 | 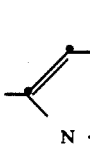 | 159–162 |
| 2.8 | 5-$SCH_3$ | H | H | H | H | H | 4 | 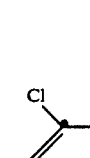 | 157–161 |

TABLE 2-continued
Intermediates of formula
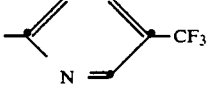
| Comp. No. | $R_1$ | $R_2$ | $R_3$ | $R_4$ | $R_6$ | $R_5$ | Position of Het | Het | M.p. [°C.] |
|---|---|---|---|---|---|---|---|---|---|
| 2.9 | 3-$CF_3$ | H | H | H | H | H | 4 | 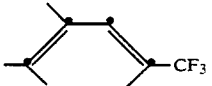 | 165–167 |
| 2.10 | 5-Cl | H | H | H | 4-Cl | H | 3 | 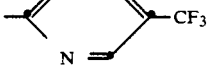 | 193–194 |
| 2.11 | 5-F | H | H | H | H | H | 4 | 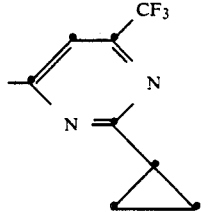 | 166–168 |
| 2.12 | 5-F | H | H | H | H | H | 4 | 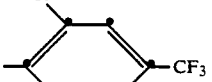 | 168–170 |
| 2.13 | 5-F | 3-F | H | H | H | H | 4 | 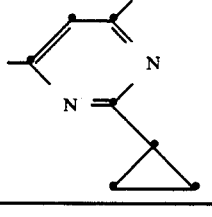 | 196–198 |
| 2.14 | 5-F | 3-F | H | H | H | H | 4 |  | 189–190 |

TABLE 3
Intermediates of formula
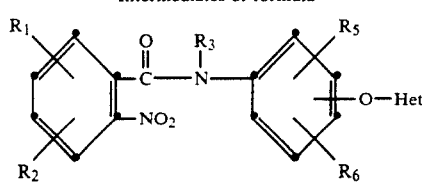
| Comp. No. | $R_1$ | $R_2$ | $R_3$ | $R_5$ | $R_6$ | Position of Het | Het | M.p. [°C.] |
|---|---|---|---|---|---|---|---|---|
| 3.1 | 5-Cl | H | H | H | H | 4 | Cl-pyridyl-CF$_3$ | 216–218 |
| 3.2 | 5-Cl | H | H | H | H | 4 | CF$_3$-pyridyl-cyclopropyl | 188–192 |
| 3.3 | 5-Cl | H | H | H | H | 4 | CF$_3$-pyridyl | 203–205 |
| 3.4 | 5-Cl | H | H | H | H | 4 | CF$_3$-pyrimidyl-C$_3$H$_9$-t | 202–203 |
| 3.5 | 4-Cl | H | H | H | H | 4 | Cl-pyridyl-CF$_3$ | 214–216 |
| 3.6 | 4-Cl | H | H | H | H | 4 | CF$_3$-pyridyl-cyclopropyl | 195–198 |
| 3.7 | 5-Cl | H | H | H | 4-Cl | 3 | Cl-pyridyl-CF$_3$ | 168–170 |

TABLE 3-continued

Intermediates of formula $$\text{R}_1, \text{R}_2 \text{-substituted phenyl-C(=O)-N(R}_3\text{)-phenyl(R}_5,\text{R}_6\text{)-O-Het, with NO}_2 \text{ ortho to C=O}$$

| Comp. No. | $R_1$ | $R_2$ | $R_3$ | $R_5$ | $R_6$ | Position of Het | Het | M.p. [°C.] |
|---|---|---|---|---|---|---|---|---|
| 3.8 | 5-SCH$_3$ | H | H | H | H | 4 | pyridyl with CF$_3$ and cyclopropyl | 204–207 |
| 3.9 | 5-SCH$_3$ | H | H | H | H | 4 | pyridyl with Cl and CF$_3$ | 221–224 |
| 3.10 | 5-F | H | H | H | H | 4 | pyrimidyl with CF$_3$ and cyclopropyl | 181–182 |
| 3.11 | 5-F | H | H | H | H | 4 | pyridyl with Cl and CF$_3$ | 206–207 |
| 3.12 | 5-F | 3-F | H | H | H | 4 | pyridyl with Cl and CF$_3$ | 217–218 |
| 3.13 | 5-F | 3-F | H | H | H | 4 | pyrimidyl with CF$_3$ and cyclopropyl | 219–220 |

2. FORMULATION EXAMPLES (THROUGHOUT, PERCENTAGES ARE BY WEIGHT)

| 2.1. Emulsifiable concentrates | a) | b) | c) |
|---|---|---|---|
| active ingredient from Table 1 | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 mols of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| 2.2. Solutions | a) | b) | c) | d) |
|---|---|---|---|---|
| active ingredient from Table 1 | 80% | 10% | 5% | 95% |
| ethylene glycol monomethyl ether | 20% | — | — | — |
| polyethylene glycol (mol. wt. 400) | — | 70% | — | — |
| N-methyl-2-pyrrolidone | — | 20% | — | — |
| epoxidised coconut oil | — | — | 1% | 5% |
| petroleum fraction (boiling range 160–190° C.) | — | — | 94% | — |

The solutions are suitable for use in the form of microdrops.

| 2.3. Granulates | a) | b) |
|---|---|---|
| active ingredient from Table 1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo. Such granulates can be admixed with the animal feed.

| 2.4. Dusts | a) | b) |
|---|---|---|
| active ingredient from Table 1 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

| 2.5. Powder mixture dispersible in water | a) | b) | c) |
|---|---|---|---|
| active ingredient from Table 1 | 25% | 50% | 75% |
| sodium lignosulfonate | 5% | 5% | — |
| oleic acid | 3% | — | 5% |
| sodium diisobutylnaphthalene-sulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 2.6. Emulsifiable concentrate | a) | b) | c) |
|---|---|---|---|
| active ingredient from Table 1 | 10% | 8% | 60% |
| octylphenol polyethylene glycol ether (4–5 moles of ethylene oxide) | 3% | 3% | 2% |
| castor oil polyethylene glycol ether (35 moles of ethylene oxide) | 4% | 5% | 4% |
| cyclohexanone | 30% | 40% | 15% |
| xylene mixture | 50% | 40% | 15% |

Emulsions of any desired concentration can be produced from this concentrate by dilution with water.

| 2.7. Dusts | a) | b) |
|---|---|---|
| active ingredient from Table 1 | 5% | 8% |
| talcum | 95% | — |
| kaolin | — | 92% |

Ready-for-use dusts are obtained by mixing the active ingredient with the carrier and grinding the mixture on a suitable mill.

| 2.8. Granulate | |
|---|---|
| active ingredient from Table 1 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 2.9. Granulate | |
|---|---|
| active ingredient from Table 1 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| 2.10. Suspension concentrate | |
|---|---|
| active ingredient from Table 1 | 40% |
| ethylene glycol | 10% |
| nonylphenol polyethylene glycol ether (15 moles of ethylene oxide) | 6% |
| sodium lignosulfonate | 10% |
| carboxymetylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

| 2.11. Pellets or boli | | |
|---|---|---|
| I | an active ingredient from Table 1 | 33.00% |
| | methylcellulose | 0.80% |
| | highly dispersed silicic acid | 0.80% |
| | cornstarch | 8.40% |
| II | crystalline lactose | 22.50% |
| | cornstarch | 17.00% |
| | microcrystalline cellulose | 16.50% |
| | magnesium stearate | 1.00% |

I The methylcellulose is stirred into water and allowed to swell; the silicic acid is stirred in and the mixture is made into a homogeneous suspension. The active ingredient and cornstarch are mixed and the aqueous suspension is incorporated into this mixture which is kneaded to a paste. The mass so obtained is granulated through a 12M sieve and dried.

II All 4 adjuvants are thoroughly mixed.

III Phases I and II are mixed together and compressed to pellets or boli.

3. BIOLOGICAL EXAMPLES

The anthelmintic activity is demonstrated by way of the following tests:

3.1. Trial with sheep infested with nematodes such as *Haemonchus contortus* and *Trichostrongylus colubriformis*

The active ingredient is administered in the form of a suspension using a stomach probe or by intraruminal injection to sheep that have previously been artificially infested with nematodes, such as Haemonchus contortus and *Trichostrongylus colubriformis*. 1 to 3 animals are used for each dose per trial. Each sheep is treated only once with a single dose.

A first evaluation is made by comparing the number of worm eggs excreted in the faeces of the sheep before and after treatment.

Seven to ten days after treatment the sheep are sacrificed and dissected. The evaluation is carried out by counting the worms remaining in the intestine after the treatment. Sheep simultaneously and similarly infested but untreated are used as a control or comparison.

Compounds from Table 1 administered to sheep in the form of a suspension at a dose of 50 mg/kg body weight or lower effect a reduction in nematode infestation of 90% or more compared with untreated but infested comparison groups. Compounds of formula I, such as, for example, No. 1.1 and 1.2, produce a reduction in nematode infestation of more than 90% even at a dose of 20 mg/kg body weight.

3.2. Trial with sheep infested with *Fasciola hepatica*

The active ingredient is administered in the form of a suspension using a stomach probe or by intraruminal injection to sheep that have previously been artificially infested with *Fasciola hepatica*. 3 animals are used for each dose per trial. Each sheep is treated only once with a single dose.

A first evaluation is made by comparing the number of worm eggs excreted in the faeces of the sheep before and after treatment.

Three to four weeks after treatment the sheep are sacrificed and dissected. The evaluation is carried out by counting the liver flukes remaining in the gall-bladder ducts after the treatment. Sheep simultaneously and similarly infested but untreated are used as a control or comparison. The difference in the number of liver flukes counted in the two groups gives the degree of effectiveness of the test compound.

Suspensions with active ingredients from Table I produce good results, that is to say a decrease in liver fluke infestation of at least 90% at a dose of 50 mg/kg body weight or lower.

What is claimed is:

1. Compounds of formula I in which
$R_1$ is hydrogen, halogen, $C_1$-$C_2$alkyl, $C_1$-$C_2$thioalkyl, $C_1$-$C_2$haloalkyl, nitro, $C_1$-$C_2$alkoxy, or the group $SO_nR$ in which R is $C_1$-$C_2$alkyl or phenyl and n is 0, 1 or 2;
$R_2$ is hydrogen, halogen, $C_1$-$C_2$alkyl, $C_1$-$C_2$haloalkyl, $C_1$-$C_2$haloalkoxy or $C_1$-$C_2$alkoxy;
$R_3$ is hydrogen or $C_1$-$C_2$alkyl;
$R_4$ is hydrogen or $C_1$-$C_2$alkyl;
$R_5$ is hydrogen, halogen or $C_1$-$C_5$alkyl;
$R_6$ is hydrogen, halogen or $C_1$-$C_5$alkyl;
$R_7$ is hydrogen, halogen, $C_1$-$C_2$alkyl, nitro, $C_1$-$C_2$haloalkyl, $C_1$-$C_2$haloalkoxy or $C_1$-$C_2$alkoxy;
$R_8$ is hydrogen, halogen, $C_1$-$C_2$alkyl, $C_1$-$C_2$haloalkyl, $C_1$-$C_2$haloalkoxy or $C_1$-$C_2$alkoxy;
$R_9$ is hydrogen, halogen, $C_1$-$C_2$alkyl, $C_1$-$C_2$haloalkyl, $C_1$-$C_2$haloalkoxy or $C_1$-$C_2$alkoxy;
$R_{10}$ is hydrogen, halogen, $C_1$-$C_6$alkyl, $C_1$-$C_2$haloalkyl, $C_1$-$C_2$alkylthio, $C_3$-$C_6$cycloalkyl or cyano;
$R_{11}$ is hydrogen, halogen, $C_1$-$C_6$alkyl, $C_1$-$C_2$haloalkyl, $C_1$-$C_2$alkylthio or $C_3$-$C_6$cycloalkyl;
$R_{12}$ is hydrogen or halogen; and
Y is =CH—; including the physiologically tolerable acid addition salts thereof.

2. A compound according to claim 1, in which
$R_1$ is hydrogen, halogen, $C_1$-$C_2$alkyl, $C_1$-$C_2$haloalkyl, nitro, $C_1$-$C_2$alkoxy, or the group $SO_nR$ in which R is $C_1$-$C_2$alkyl or phenyl and n is 0, 1 or 2; and $R_2$ to $R_{12}$ and Y are as defined in claim 1.

3. A compound according to claim 1, in which
$R_1$, $R_2$, $R_3$, $R_4$, $R_7$, $R_8$, $R_9$, $R_{12}$ and Y are as defined for formula I;
$R_5$ is hydrogen, halogen or $C_1$-$C_3$alkyl;
$R_6$ is hydrogen, halogen or $C_1$-$C_3$alkyl;
$R_{10}$ is hydrogen, halogen, $C_1$-$C_4$alkyl, $C_1$-$C_2$haloalkyl, $C_1$-$C_2$alkylthio, cyclopropyl or cyano; and
$R_{11}$ is hydrogen, halogen, $C_1$-$C_4$alkyl, $C_1$-$C_2$haloalkyl, $C_1$-$C_2$alkylthio or cyclopropyl; including the physiologically tolerable acid addition salts thereof.

4. A compound according to claim 2, in which
$R_1$ is hydrogen, halogen, methyl, methoxy or thiomethyl;
$R_2$ is hydrogen, methyl or halogen;
$R_3$ is hydrogen, methyl or ethyl;
$R_4$ is hydrogen, methyl or ethyl;
$R_5$ is hydrogen, halogen or $C_1$-$C_4$alkyl;
$R_6$ is hydrogen, halogen or $C_1$-$C_4$alkyl;
$R_7$ is hydrogen, halogen, methyl, methoxy, $CF_3$ or nitro;
$R_8$ is hydrogen or halogen;
$R_9$ is hydrogen, halogen, $C_1$-$C_2$alkyl, $C_1$-$C_2$haloalkyl, $C_1$-$C_2$haloalkoxy or $C_1$-$C_2$alkoxy;

$R_{10}$ and $R_{11}$, independently of one another, are each hydrogen, halogen, $C_1$–$C_4$alkyl, methylthio, trifluoromethyl, $CF_2CCl_2F$, cyclopropyl or cyano;

$R_{12}$ is hydrogen or halogen; and

Y is =CH—, wherein the pyridinoxy substituent is bonded by way of the 3- or 4-position of the phenyl ring.

5. A compound according to claim 1, in which $R_1$ is 5-halogen or 4-halogen;

$R_2$ is hydrogen;

$R_3$ is hydrogen or $C_1$–$C_2$alkyl;

$R_4$ is hydrogen or $C_1$–$C_2$alkyl;

$R_5$ is hydrogen, halogen or $C_1$–$C_5$alkyl;

$R_6$ is hydrogen, halogen or $C_1$–$C_5$alkyl;

$R_7$ is hydrogen, halogen, $C_1$–$C_2$alkyl, nitro, $C_1$–$C_2$haloalkyl, $C_1$–$C_2$haloalkoxy or $C_1$–$C_2$alkoxy;

$R_8$ is hydrogen, halogen, $C_1$–$C_2$alkyl, $C_1$–$C_2$haloalkyl, $C_1$–$C_2$haloalkoxy or $C_1$–$C_2$alkoxy;

$R_9$ is hydrogen, halogen, $C_1$–$C_2$alkyl, $C_1$–$C_2$haloalkyl, $C_1$–$C_2$haloalkoxy or $C_1$–$C_2$alkoxy;

$R_{10}$ is hydrogen, halogen, $C_1$–$C_6$alkyl, $C_1$–$C_2$haloalkyl, $C_1$–$C_2$alkylthio, $C_3$–$C_6$cycloalkyl or cyano;

$R_{11}$ is hydrogen, halogen, $C_1$–$C_6$alkyl, $C_1$–$C_2$haloalkyl, $C_1$–$C_2$alkylthio or $C_3$–$C_6$cycloalkyl;

$R_{12}$ is hydrogen or halogen; and

Y is =CH—; including the physiologically tolerable acid addition salts thereof.

6. A compound according to claim 5, in which $R_1$ is 5-chlorine or 4-chlorine;

$R_2$ is hydrogen;

$R_3$ is hydrogen, methyl or ethyl;

$R_4$ is hydrogen, methyl or ethyl;

$R_5$ is hydrogen, halogen or $C_1$–$C_4$alkyl;

$R_6$ is hydrogen, halogen or $C_1$–$C_4$alkyl;

$R_7$ is hydrogen, halogen, methyl, methoxy, $CF_3$ or nitro;

$R_8$ is hydrogen or halogen;

$R_9$ is hydrogen, halogen, $C_1$–$C_2$alkyl, $C_1$–$C_2$haloalkyl, $C_1$–$C_2$haloalkoxy or $C_1$–$C_2$alkoxy;

$R_{10}$ and $R_{11}$, independently of one another, are each hydrogen, halogen, $C_1$–$C_4$alkyl, methylthio, trifluoromethyl, $CF_2CCl_2F$, cyclopropyl or cyano;

$R_{12}$ is hydrogen or halogen; and

Y is =CH—, wherein the pyridinoxy substituent is bonded by way of the 3- or 4-position of the phenyl ring.

7. A compound according to claim 1, selected from the series:

5-chloro-2-[(4-chlorophenylsulfonyl)-amino]-benzoic acid [4-(4-trifluoromethyl-6-cyclopropylpyrimidin-2-yloxy)-anilide];

5-chloro-2-[(4-chlorophenylsulfonyl)-amino]-benzoic acid [4-(3-chloro-5-trifluoromethylpyridin-2-yloxy)-anilide];

5-chloro-2-[(4-chlorophenylsulfonyl)-amino]-benzoic acid [4-(4-trifluoromethylpyridin-2-yloxy)-anilide];

3,5-dichloro-2-[(4-chlorophenylsulfonyl)-amino]-benzoic acid [4-(5-trifluoromethylpyridin-2-yloxy)-anilide].

8. The compound 4-chloro-2-[(4-chlorophenylsulfonyl)-amino]-benzoic acid [4-(3-chloro-5-trifluoromethylpyridin-2-yloxy)-anilide] according to claim 1.

9. A composition comprising an anthelminitically effective amount of a compound according to claim 1 together with a physiologically tolerable, inert formulation adjuvant.

10. A method of controlling helminths in a warm-blooded animal, which comprises administering prophylactically or curatively to the warm-blooded animal an anthelmintically effective amount of a compound of according to claim 1.

11. A composition comprising an anthelmintically effective amount of a compound according to claim 2 together with a physiologically tolerable, inert formulation adjuvant.

12. A composition comprising an anthelmintically effective amount of a compound according to claim 3 together with a physiologically tolerable, inert formulation adjuvant.

13. A composition comprising an anthelminitically effective amount of a compound according to claim 5 together with a physiologically tolerable, inert formulation adjuvant.

14. A composition comprising an anthelmintically effective amount of a compound according to claim 6 together with a physiologically tolerable, inert formulation adjuvant.

15. A composition comprising an anthelmintically effective amount of a compound according to claim 7 together with a physiologically tolerable, inert formulation adjuvant.

16. A method of controlling helminths in a warm-blooded animal, which comprises administering prophylactically or curatively to the warm-blooded animal an anthelmintically effective amount of a compound according to claim 2.

17. A method of controlling helminths in a warm-blooded animal, which comprises administering prophylactically or curatively to the warm-blooded animal an anthelmintically effective amount of a compound according to claim 3.

18. A method of controlling helminths in a warm-blooded animal, which comprises administering prophylactically or curatively to the warm-blooded animal an anthelmintically effective amount of a compound according to claim 5.

19. A method of controlling helminths in a warm-blooded animal, which comprises administering prophylactically or curatively to the warm-blooded animal an anthelmintically effective amount of a compound according to claim 6.

20. A method of controlling helminths in a warm-blooded animal, which comprises administering prophylactically or curatively to the warm-blooded animal an anthelmintically effective amount of a compound according to claim 7.

* * * * *